United States Patent
Green et al.

(10) Patent No.: US 8,253,940 B1
(45) Date of Patent: Aug. 28, 2012

(54) UV-IR RANGE VARIABLE ANGLE SPECTROSCOPIC ELLIPSOMETER

(75) Inventors: Steven E. Green, Lincoln, NE (US); Gerald T. Cooney, Lincoln, NE (US); Martin M. Liphardt, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 198 days.

(21) Appl. No.: 12/806,870

(22) Filed: Aug. 23, 2010

Related U.S. Application Data

(60) Provisional application No. 61/274,905, filed on Aug. 24, 2009.

(51) Int. Cl.
*G01J 4/00* (2006.01)

(52) U.S. Cl. ............... 356/369; 356/364; 359/641

(58) Field of Classification Search ............ 356/364, 356/369, 367; 250/339.11, 341.8
See application file for complete search history.

(56) References Cited

U.S. PATENT DOCUMENTS

| | | | | |
|---|---|---|---|---|
| 4,656,331 A | * | 4/1987 | Lillquist et al. | 219/121.47 |
| 4,713,824 A | * | 12/1987 | Heller | 372/99 |
| 5,373,359 A | * | 12/1994 | Woollam et al. | 356/328 |
| 5,706,212 A | | 1/1998 | Thompson et al. | 702/85 |
| 5,910,842 A | | 6/1999 | Piwonka-Corle et al. | 356/369 |
| 5,917,594 A | | 6/1999 | Norton | 356/327 |
| 6,323,946 B1 | | 11/2001 | Norton | 356/327 |
| 6,734,967 B1 | | 5/2004 | Piwonka-Corle et al. | 356/369 |
| 6,879,449 B2 | | 4/2005 | Wang et al. | 359/785 |
| 6,902,326 B1 | | 6/2005 | Ames et al. | 385/60 |
| 7,075,630 B2 | | 7/2006 | Meeks et al. | 356/73 |
| 7,075,650 B1 | | 7/2006 | Johs et al. | 356/369 |
| 7,158,231 B1 | * | 1/2007 | Woollam et al. | 356/369 |
| 7,184,145 B2 | | 2/2007 | Amary et al. | 356/369 |
| 7,433,034 B1 | * | 10/2008 | Huang | 356/237.5 |
| 7,492,455 B1 | | 2/2009 | Johs et al. | 356/369 |
| 7,557,919 B2 | | 7/2009 | Fukue | 356/369 |
| 2004/0218261 A1 | * | 11/2004 | Tuunanen | 359/364 |
| 2009/0257118 A1 | * | 10/2009 | Heritier et al. | 359/399 |

OTHER PUBLICATIONS

Ben-Zion Dekel and Abraham Katzir, "Graded-index silver chlorobromide fibers for the mid-infrared," Appl. Opt. 44, 3343-3348 (2005).*

W.M. Haynes (Editor-in-Cheif), "CRC Handbook of Chemistry and Physics", $92^{nd}$ Edition Internet Version, 2011-2012, pp. 10-83 to 10-84.*

W.M. Haynes (Editor-in-Chief), "CRC Handbook of Chemistry and Physics", $92^{nd}$ Edition Internet Version, 2011-2012, p. 10-238.*

* cited by examiner

*Primary Examiner* — Jessica Stultz
*Assistant Examiner* — Shawn Decenzo
(74) *Attorney, Agent, or Firm* — James D. Welch

(57) ABSTRACT

An ellipsometer, polarimeter, reflectometer, spectrophotometer or scatterometer system for use in the UV and infrared range of wavelengths, characterized by the combination of a fiber optic capable of transmitting wavelengths from below 2.2 micron up to at least 3.5 microns, and a beam collimator formed from a combination of two off-axis concave astigmatism reducing spherical mirrors capable of operating between about 190 nm up to 5.5 microns.

12 Claims, 4 Drawing Sheets

UV-IR RANGE VARIABLE ANGLE SPECTROSCOPIC ELLIPSOMETER

This Application Claims Benefit of Provisional Application 61/274,905 Filed Aug. 24, 2009.

TECHNICAL FIELD

The present invention is a reflectometer, spectrophotometer, ellipsometer, polarimeter or scatterometer system, and more particularly is a reflectometer, spectrophotometer, ellipsometer, polarimeter or scatterometer system for use in the infrared range of wavelengths, characterized by the combination of a fiber optic capable of transmitting wavelengths from below 2.2 micron up to at least 3.5 microns and a beam collimator which comprises a combination of two off-axis concave spherical mirrors.

BACKGROUND

A Patent to Thompson and Johs, U.S. Pat. No. 5,706,212 describes an ellipsometer or polarimeter for use at infrared wavelengths. Described is a system comprising a source of a beam of electromagnetic wavelengths, a polarizer means, a stage for supporting a sample system, an analyzer means and a detector system. Further included is at least one compensator positioned between the source and said stage for supporting a sample or between said stage for supporting a sample and the detector. The preferred embodiment involves use of a dual rhomb shaped compensator which causes essentially no deviation of a beam passing therethrough, even when the compensator is caused to rotate about the beam locus. A Patent to Fukue, U.S. Pat. No. 7,557,919 is identified as it uses concave mirrors to direct beams in an ellipsometer. A Patent to Ames et al., U.S. Pat. No. 6,902,326 describes a reflective off-axis optical apparatus such as a collimator. A Patent to Zawaideh et al. describes an optical metrology system involving two off-axis paraboloid mirrors. A Patent to Wang et al., U.S. Pat. No. 6,879,449 is disclosed as it turned up in a search using key words "off axis reflective" and "ellipsometer", but is not believed to be particularly relevant. Additional searching was performed using keywords "ellipsometer" and "collimation and provided U.S. Pat. Nos. 7,075,650 and 7,492,455 to Johs et al. and 7,184,145 to Amary et al.

It is interesting to note that searching with keywords "reflective collimation" and KLA, (ie. KLA-Tencor), turned up no Patents. KLA Tencor is acknowledged as having Patents to ellipsometers that use reflective focusing. Some examples of KLA Patents are: U.S. Pat. Nos. 6,734,967 and 5,910,842 to Piwonka-Corle et al.; 6,323,946 and 5,917,594 to Norton, (which do disclose a single mirror reflection beams collimation); and 7,075,630 to Meeks et al.

Even in view of the prior art, need remains for a reflectometer, spectrophotometer, ellipsometer, polarimeter or scatterometer system for use in the infrared range of wavelengths.

DISCLOSURE OF THE INVENTION

A general present invention system is a spectroscopic reflectometer, spectrophotometer, ellipsometer or polarimeter system comprises:
- an arc lamp source of a beam of electromagnetic radiation comprising wavelengths between less than 2.2 microns and at least 3.5 microns;
- a monochromator;
- a fiber optic capable of transmitting wavelengths from below 2.2 microns up to at least 3.5 microns;
- a beam collimator comprising a combination of two off-axis concave spherical mirrors arranged such that total off-axis astigmatism caused within the beam collimator is substantially canceled over a range of at least 190 nm-5.5 microns;
- a sample supporting stage; and
- a detector system of wavelengths between less than 2.2 microns and at least 3.5 microns.

The source of electromagnetic radiation provides a beam comprising wavelengths between less than 2.2 microns and at least 3.5 microns, said monochromator selects a wavelength and passes it to said fiber optic, said beam then is collimated by said beam collimator and interacts with a sample on said sample supporting stage and enters said detector system. Said spectroscopic reflectometer, spectrophotometer, ellipsometer or polarimeter system being distinguished by the combination of the fiber optic capable of transmitting wavelengths from below 2.2 micron up to at least 3.5 microns and the beam collimator which comprises a combination of two off-axis concave spherical mirrors.

A preferred present invention spectroscopic reflectometer or spectrophotometer ellipsometer or polarimeter system further comprises:
- means for varying the positions of the source and detector system;

such that in use the source and detector systems are positioned to effect a desired angle-of-incidence of a beam of electromagnetic radiation exiting said arc lamp source onto a sample on said sample supporting stage and then enter said detector system.

A more specific present invention system is a rotating analyzer spectroscopic ellipsometer or polarimeter system comprising:
- a polarization state generator comprising:
  - an arc lamp source of a beam of electromagnetic radiation comprising wavelengths between less than 2.2 microns and at least 3.5 microns;
  - a monochromator;
  - a fiber optic capable of transmitting wavelengths from below 2.2 microns up to at least 3.5 microns;
  - a beam collimator comprising a combination of two off-axis concave spherical mirrors arranged such that total off-axis astigmatism caused within the beam collimator is substantially canceled over a range of at least 190 nm-5.5 microns;
  - a rotatable polarizer; and
  - optionally a variable retarder;
- a sample supporting stage; and
- a polarization state detector comprising:
  - a rotating analyzer;
  - a detector system of wavelengths between less than 2.2 microns and at least 3.5 microns.

Said rotating analyzer spectroscopic ellipsometer or polarimeter system further comprises means for varying the positions of the source and detector system; such that in use the source and detector systems are positioned to effect a desired angle-of-incidence of incidence of a beam of electromagnetic radiation exiting said polarization state generator onto a sample on said sample supporting stage, and then enter said detector system. Further, the source of electromagnetic radiation provides a beam comprises wavelengths between less than 2.2 microns and at least 3.5 microns, and said monochromator selects a wavelength and passes it to said rotatable polarizer via said fiber optic, said beam then being collimated by said beam collimator and optionally passing through said optional variable retarder, then interacting with a sample on said sample supporting stage, and passes through said rotating analyzer and enters said detector system.

Said rotating analyzer spectroscopic ellipsometer or polarimeter system can comprise a detector system comprising at least two detectors, one thereof being capable of detecting wavelengths below about 2.2 microns, and the other being capable of detecting wavelengths between about 2.2 microns and 3.5 microns, said two detectors having at least some overlap of wavelength detection range.

Said rotating analyzer spectroscopic ellipsometer or polarimeter system detector of wavelengths below about 2.2 microns can be selected from the group consisting of:
Si;
PbSi;
InGaAs;
Ge; and
HgCdTe;
InSb;
InAs;
PbAs;
PbSe;
PtSi;
PV MCT;
IrSi;
PbS;
InAs;
MCT;
and the detector of wavelengths up to at least 3.5 microns can be selected from the group consisting of:
InSb;
MCT;
PbSe;
PV MCT;
Ge:Hg;
Ge:Zn;
IrSi;
Ge:Cd;
Ge:Cu;
Ge:Au;
HgCdTe.
HgCdTeTe;
InSb; and
MCT.

Said rotating analyzer spectroscopic ellipsometer or polarimeter system detector of wavelengths longer than about 3.5 microns can further comprises thermal electric or liquid nitrogen cooling.

Further, said rotating analyzer spectroscopic ellipsometer or polarimeter system can apply a fiber optic which is composed of:

$ZrF_4$—$BaF_2$—$LaF_3$—$AlF_3$—$NaF$;

or a fiber composed of:
AgBrCl; or
AsGeTeSe;
which transmits wavelengths up to at least 3.5 microns.

Said rotating analyzer spectroscopic ellipsometer or polarimeter beam collimator preferable comprises a combination of two off-axis concave spherical mirrors arranged in a manner such that total off-axis astigmatism caused within the beam collimator is substantially canceled.

A present invention system can also comprise a rotating polarizer spectroscopic ellipsometer or polarimeter system comprising:
a polarization state generator comprising:
an arc lamp source of a beam of electromagnetic radiation comprising wavelengths between less than 2.2 microns and at least 3.5 microns;
a monochromator;
a fiber optic capable of transmitting wavelengths from below 2.2 microns up to at least 3.5 microns;
a beam collimator comprising a combination of two off-axis concave spherical mirrors arranged such that total off-axis astigmatism caused within the beam collimator is substantially canceled over a range of at least 190 nm-5.5 microns;
a rotating polarizer; and
optionally a variable retarder;
a sample supporting stage; and
a polarization state detector comprising:
a rotatable analyzer;
a detector system of wavelengths between less than 2.2 microns and at least 3.5 microns.

Said spectroscopic ellipsometer or polarimeter system further comprises means for varying the positions of the source and detector system such that in use the source and detector systems are positioned to effect a desired angle-of-incidence of incidence of a beam of electromagnetic radiation exiting said polarization state generator onto a sample on said sample supporting stage, and then enter said detector system. Further, the source of electromagnetic radiation provides a beam comprising wavelengths between less than 2.2 microns and at least 3.5 microns, said monochromater selects a wavelength and passes it to said rotating polarizer via said fiber optic, said beam then being collimated by said beam collimator and optionally passing through said optional variable retarder, then interacts with a sample on said sample supporting stage, and passes through said analyzer and enters said detector system.

Said rotating polarizer spectroscopic ellipsometer or polarimeter system can provide that the detector system comprise one or more detectors, (eg. one detector being capable of detecting wavelengths below about 2.2 microns, and the another being capable of detecting wavelengths between about 2.2 microns and 3.5 microns, said two detectors having at least some overlap of wavelength detection range).

Said rotating polarizer spectroscopic ellipsometer or polarimeter system can comprise a detector of wavelengths below about 2.2 microns which is selected from the group consisting of:
Si;
PbSi;
InGaAs;
Ge; and
HgCdTe;
InSb;
InAs;
PbAs;
PbSe;
PtSi;
PV MCT;
IrSi;
PbS;
InAs;
MCT;

and the detector of wavelengths up to at least 3.5 microns can be selected from the group consisting of:
InSb;
MCT;
PbSe;
PV MCT;
Ge:Hg;
Ge:Zn;
IrSi;
Ge:Cd;
Ge:Cu;
Ge:Au;
HgCdTe.
HgCdTeTe;
InSb; and
MCT.

Said rotating polarizer spectroscopic ellipsometer or polarimeter system can involve that the detector of wavelengths longer than about 3.5 microns further comprises thermal electric or liquid nitrogen cooling.

Said rotating polarizer spectroscopic ellipsometer or polarimeter system can involve a fiber optic which is composed of:

$$ZrF_4\text{---}BaF_2\text{---}LaF_3\text{---}AlF_3\text{---}NaF;$$

or a fiber composed of:
AgBrCl; or
AsGeTeSe;
which transmits wavelengths up to at least 3.5 microns.

Said rotating polarizer spectroscopic ellipsometer or polarimeter system can provide that the beam collimator comprises a combination of two off-axis concave spherical mirrors arranged in a manner such that total off-axis astigmatism caused within the beam collimator is substantially canceled.

A present invention system can also comprise a spectroscopic reflectometer or spectrophotometer system comprising:
  an arc lamp source of a beam of electromagnetic radiation comprising wavelengths between less than 2.2 microns and at least 3.5 microns;
  a monochromator;
  a fiber optic capable of transmitting wavelengths from below 2.2 microns up to at least 3.5 microns;
  a beam collimator comprising a combination of two off-axis concave spherical mirrors arranged such that total off-axis astigmatism caused within the beam collimator is substantially canceled over a range of at least 190 nm-5.5 microns;
  a sample supporting stage; and
  a detector system of wavelengths between less than 2.2 microns and at least 3.5 microns.

Said spectroscopic reflectometer or spectrophotometer system can further comprise means for varying the positions of the source and detector system such that in use the source and detector systems are positioned to effect a desired angle-of-incidence of incidence of a beam of electromagnetic radiation exiting said polarization state generator onto a sample on said sample supporting stage and enters said detector system.

Further, the source of electromagnetic radiation can provide a beam comprising wavelengths between less than 2.2 microns and at least 3.5 microns, said monochromater selects a wavelength and passes it to said fiber optic, said beam then being collimated by said beam collimator and interacting with a sample on said sample supporting stage and enters said detector system.

Said detector system can comprise two detectors, one thereof being capable of detecting wavelengths below about 2.2 microns, and the other being capable of detecting wavelengths between about 2.2 microns and 3.5 microns, said two detectors having at least some overlap of wavelength detection range.

Said spectroscopic reflectometer or spectrophotometer system can involve that the detector of wavelengths below about 2.2 microns is selected from the group consisting of:
Si;
PbSi;
InGaAs;
Ge; and
HgCdTe;
InSb;
InAs;
PbAs;
PbSe;
PtSi;
PV MCT;
IrSi;
PbS;
InAs;
MCT;
and the detector of wavelengths up to at least 3.5 microns is selected from the group consisting of:
InSb;
MCT;
PbSe;
PV MCT;
Ge:Hg;
Ge:Zn;
IrSi;
Ge:Cd;
Ge:Cu;
Ge:Au;
HgCdTe.
Si;
InGaAs;
Ge; and
HgCdTe;
InSb;
InAs; and
MCT.

Said spectroscopic reflectometer or spectrophotometer system can involve that the detector of wavelengths longer than about 3.5 microns further comprises thermal electric or liquid nitrogen cooling.

Said spectroscopic reflectometer or spectrophotometer system can involve a fiber optic which is composed of:

$$ZrF_4\text{---}BaF_2\text{---}LaF_3\text{---}AlF_3\text{---}NaF;$$

or a fiber composed of:
AgBrCl; or
AsGeTeSe;
which transmits wavelengths up to at least 3.5 microns.

Said present invention spectroscopic reflectometer or spectrophotometer system can provide that the beam collimator comprise a combination of two off-axis concave spherical mirrors arranged in a manner such that total off-axis astigmatism caused within the beam collimator is substantially canceled.

In all cases above:
  the terminology "at least 3.5 microns" can be interpreted to mean "up to at least 5.0 microns";
  the two concave spherical mirrors can have reflective surfaces protected by any functional coating;

the two concave spherical mirrors can have reflective surfaces protected by a coating selected from the group:
aluminum;
SiO2; and
gold.

The present invention will be better understood by reference to the Detailed Description Section of this Specification in combination with the Drawings.

DETAILED DESCRIPTION

Figure 1:
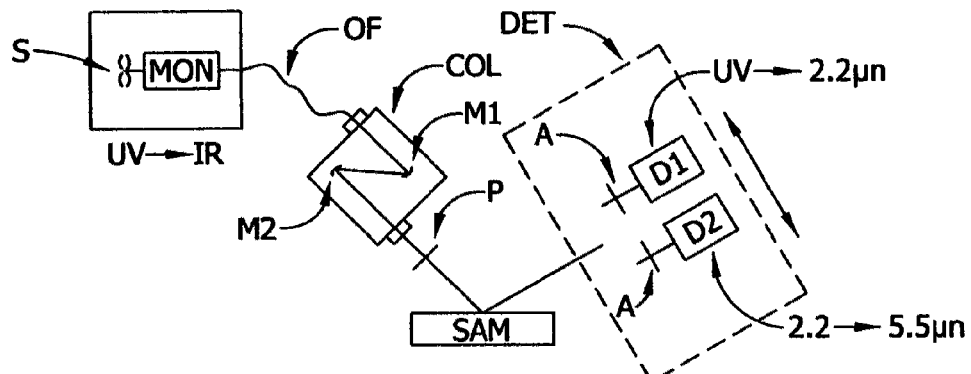
FIG. 1, there is shown a demonstrative present invention system.
Figure 2:
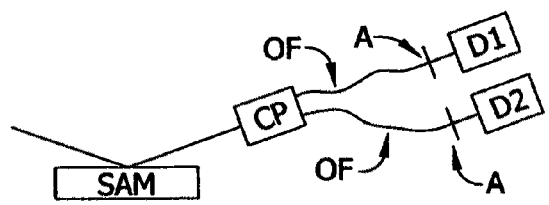
FIG. 2 is included to show that a Coupler (CP) can be used to direct a beam reflecting from the Sample (SM) to Optical Fibers, (OF) which direct it into Detector (D1) and/or (D2).

Turning now to FIG. 1, there is shown a demonstrative present invention system. Shown are a Source (S) and Monochromator (MON) for providing a desired wavelength in the UV-IR range. (Note, the monochromater can be located anywhere between the Source (S) and Detector (DET)). Also shown are a Collimator (COL) which is comprised of two off-axis Spherical Mirrors (M1) (M2) arranged such that astigmatism entered to a beam of electromagnetic radiation by interaction with one thereof, is canceled by interaction with the other thereof. (An acronym for the Collimator construction is "SMART" standing for "Spherical Mirror Astigmatism Reducing Twins"). Shown next in the sequence of elements is a Polarizer (P), followed by a Sample (SAM) and a Detector System (DET). Note that the Detector system is actually a system of two Detectors (D1) (D2), each of which have an Analyzer associated therewith. In use one of the Detectors (D21) (D2) is positioned to receive a beam reflected from the Sample (SAM). Detector (D1) is preferably selected to be sensitive to wavelengths from the UV-2.2 microns, which D2) is sensitive to wavelengths between about 2.2 to 5.5 microns. FIG. 2 is included to show that a Coupler (CP) can be used to direct the beam reflecting from the Sample (SM) to Optical Fibers (OF) which direct it into Detector (D1) and/or (D2).

Figure 3:
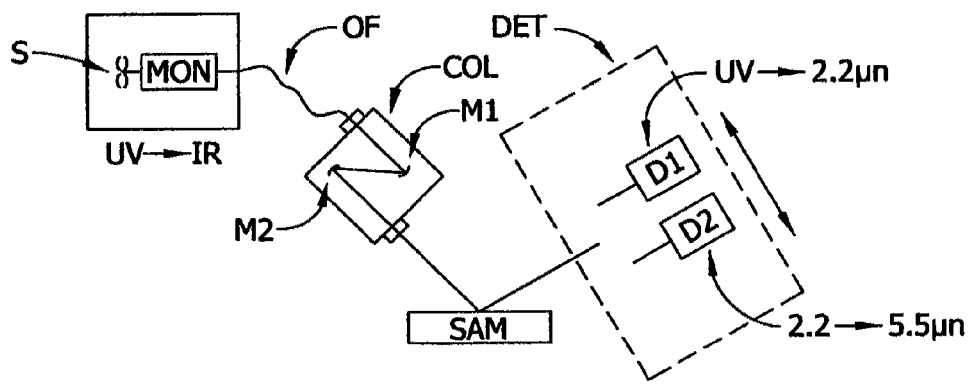
FIGS. 3 and 4 are similar to FIGS. 1 and 2, except that beam polarizing elements are not present.
Figure 4:
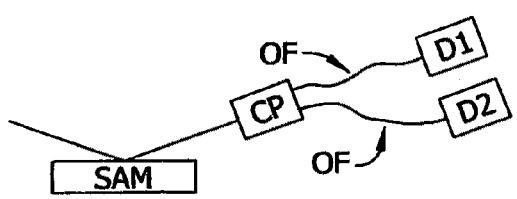

FIGS. 3 and 4 are similar to FIGS. 1 and 2, except that beam polarizing elements are not present. This demonstrates that the present invention system can be applied as a Reflectometer or Spectrophotometer.

Figure 5A:
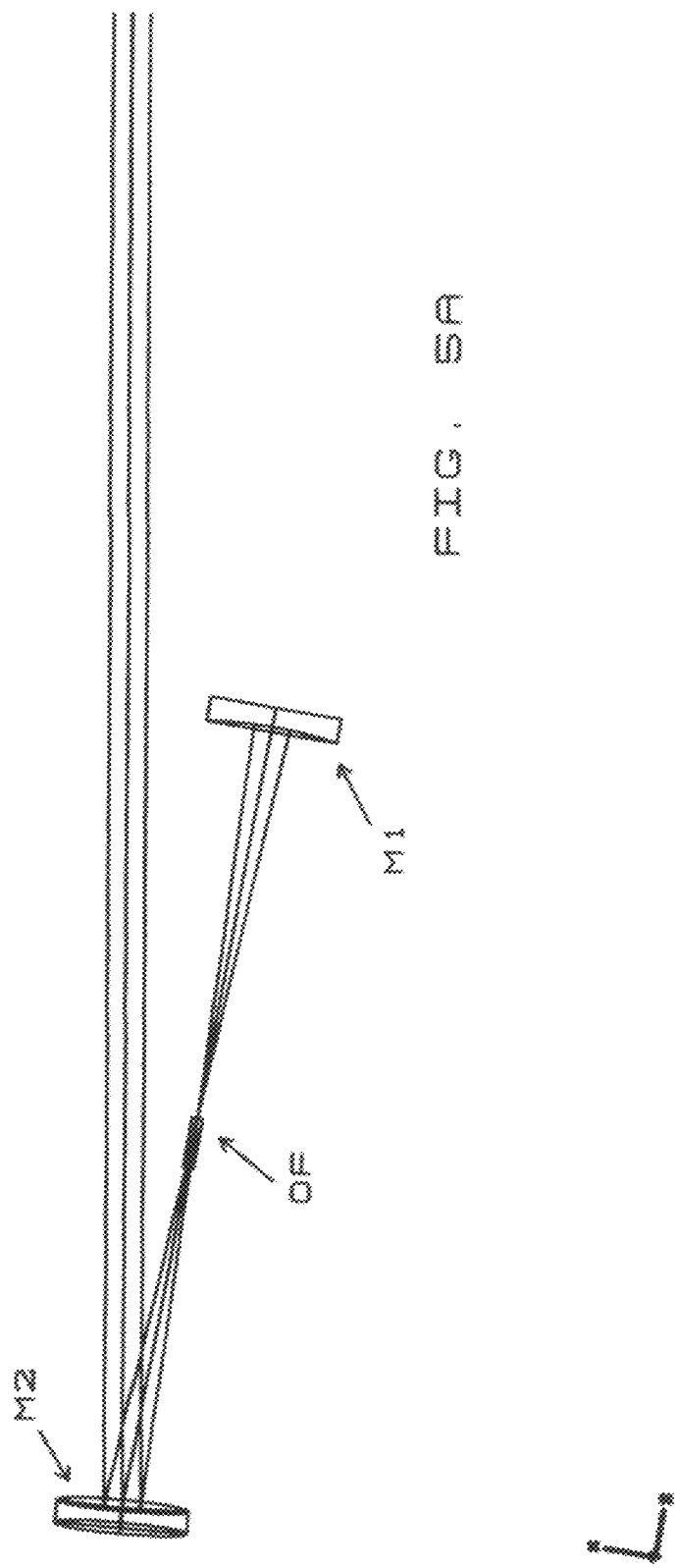
FIGS. 5a-5c demonstrate Mirror (M1) (M2) configurations for the Collimator (COL) shown in FIGS. 1 and 3.
Figure 5B:
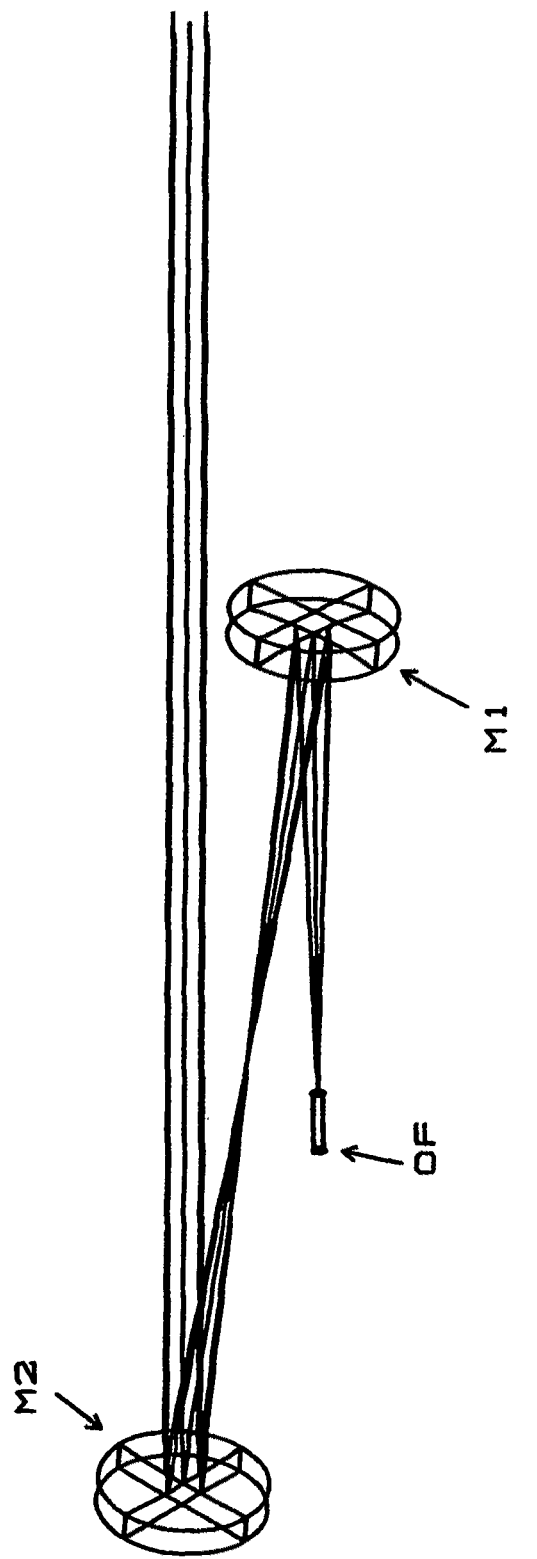
Figure 5C:
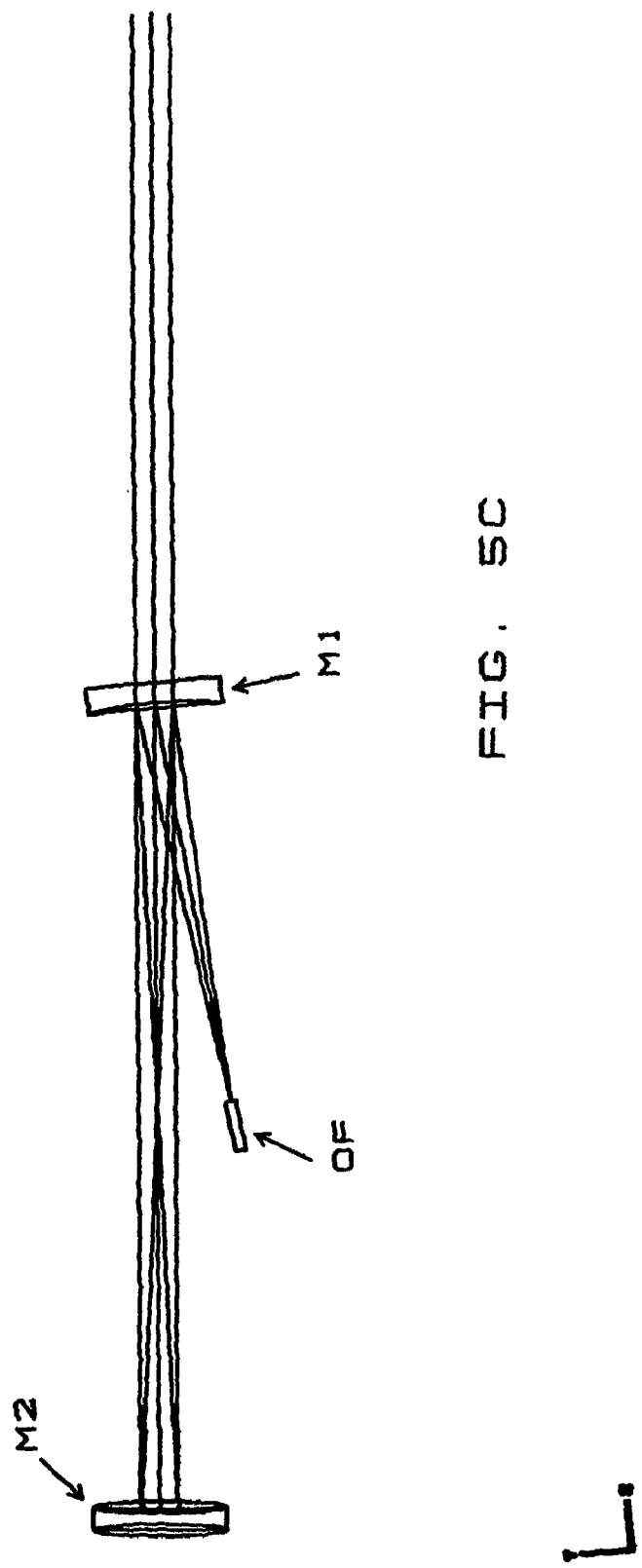

FIGS. 5a-5c demonstrate Mirror (M1) (M2) configurations for the Collimator (COL) shown in FIGS. 1 and 3. Note that the focal points are intermediate to the Mirrors (M1) and (M2) and that the end of the Optical Fiber (OF) is at a distance from (M1) which is the same as said focal length. It is believed that the Collimator (COL) design in new and novel per se., and particularly so as applied in present invention ellipsometers, polarimeters, reflectometers, spectrophotometers and scatterometers. The Collimators shown are capable of passing wavelengths from at least 190 nm to 5.5 microns, (ie. UV, Visible and IR wavelengths and preferably down to 130 nm). In combination with the use of an Optical Fiber (OF) capable of passing wavelengths in the UV-IR bands, it is believed the present invention discloses Patentable material.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A spectroscopic reflectometer, spectrophotometer, ellipsometer, polarimeter or scatterometer system comprising:
    an arc lamp source (S) of a beam of electromagnetic radiation comprising wavelengths between UV wavelengths and 3.5 microns;
    a monochromator (MON);
    a fiber optic (OF) capable of transmitting wavelengths from UV wavelengths up to 3.5 microns;
    a beam collimator (COL) comprising a combination of two off-axis concave spherical mirrors (M1) (M2) arranged such that total off-axis astigmatism caused within the beam collimator is substantially canceled over a range of at least 190 nm-5.5 microns, said mirrors (M1) (M2) being positioned so that their focal points are intermediate therebetween, and said beam collimator comprising provision for receiving an end of said fiber optic (OF) in use which positions said end of said fiber optic (OF) at a distance from said concave spherical mirror (M1) equal to a focal length of said concave spherical mirror (M1);
    said fiber optic (OF) providing a path for wavelengths between said UV wavelengths up to 3.5 microns provided by said arc-lamp source (S), between said monochromator (MON) and beam collimator (COL);
    said spectroscopic reflectometer, spectrophotometer, ellipsometer, polarimeter or scatterometer system also comprising
        a sample supporting stage; and
        at least one detector system of wavelengths between UV wavelengths and 3.5 microns;
    and such that the source of electromagnetic radiation provides a beam comprising wavelengths between UV wavelengths and 3.5 microns, said monochromater selects a wavelength and passes said wavelength, via said fiber optic, to said beam collimator which collimates said beam and directs said beam to interact with a sample on said sample supporting stage, then enter said detector system.

2. A spectroscopic reflectometer or spectrophotometer ellipsometer, polarimeter or scatterometer system as in claim 1, which further comprises:
    means for varying the positions of the source and detector system;
    such that in use the source and detector systems are positioned to affect a desired angle-of-incidence of a beam of electromagnetic radiation exiting said arc lamp source onto a sample on said sample supporting stage and then enter said detector system.

3. A spectroscopic reflectometer or spectrophotometer ellipsometer, polarimeter or scatterometer system as in claim 1, in which said at least one detector system comprises at least two detectors, one thereof being capable of detecting wavelengths below 2.2 microns, and the other being capable of detecting wavelengths between about 2.2 microns and 3.5 microns, said two detectors having at least some overlap of wavelength detection range.

4. A spectroscopic reflectometer or spectrophotometer ellipsometer, polarimeter or scatterometer system as in claim 2, in which the detector of wavelengths below 2.2 microns is selected from the group consisting of:
    Si;
    PbSi;
    InGaAs;

Ge; and
HgCdTe;
InSb;
InAs;
PbAs;
PbSe;
PtSi;
PV MCT;
IrSi;
PbS;
InAs;
MCT;
and the detector of wavelengths between 2.2 microns and 3.5 microns is selected from the group consisting of:
InSb;
MCT;
PbSe;
PV MCT;
Ge:Hg;
Ge:Zn;
IrSi;
Ge:Cd;
Ge:Cu;
Ge:Au;
HgCdTe;
HgCdTeTe;
InSb; and
MCT.

5. A spectroscopic reflectometer, spectrophotometer, ellipsometer, polarimeter or scatterometer system as in claim 4, in which the detector of wavelengths between 2.2 microns and 3.5 microns further comprises thermal electric or liquid nitrogen cooling.

6. A spectroscopic reflectometer, spectrophotometer, ellipsometer, polarimeter or scatterometer system as in claim 1, in which the fiber optic is composed of a selection from the group consisting of:

$ZrF_4$—$BaF_2$—$LaF_3$—$AlF_3$—$NaF$;

Ag—Br—Cl; and

As—Ge—Te—Se;

which transmits wavelengths up to 3.5 microns.

7. A spectroscopic reflectometer, spectrophotometer, ellipsometer or polarimeter system as in claim 1 in which the two concave spherical mirrors have reflective surfaces protected by a coating.

8. A spectroscopic reflectometer, spectrophotometer, ellipsometer or polarimeter system as in claim 7 in which the coating is a selection from the group:
aluminum;
SiO2; and
gold.

9. A spectroscopic reflectometer, spectrophotometer, ellipsometer or polarimeter system as in claim 1 which further comprises a polarizer before said a sample supporting stage and an analyzer thereafter and in which the system is a spectroscopic ellipsometer or polarimeter system.

10. A spectroscopic reflectometer, spectrophotometer, ellipsometer or polarimeter system as in claim 9 in which said polarizer rotates and the system is a rotating polarizer spectroscopic ellipsometer or polarimeter system.

11. A spectroscopic reflectometer, spectrophotometer, ellipsometer or polarimeter system as in claim 9 in which said analyzer rotates and the system is a rotating analyzer spectroscopic ellipsometer or polarimeter system.

12. A beam collimator (COL) comprising a combination of two off-axis concave spherical mirrors (M1) (M2) arranged such that total off-axis astigmatism caused within the beam collimator is substantially canceled over a range of at least 190 nm-5.5 microns, said mirrors (M1) (M2) being positioned so that their focal points are intermediate therebetween, and said beam collimator comprising provision for receiving an end of said fiber optic (OF) in use which positions said end of said fiber optic (OF) at a distance from said concave spherical mirror (M1) equal to a focal length of said concave spherical mirror (M1);
said fiber optic (OF) providing a path for wavelengths between said UV wavelengths up to 3.5 microns provided by a source (S) of electromagnetic radiation wavelengths.

* * * * *